United States Patent
Dorman

[19]

[11] Patent Number: 5,921,777
[45] Date of Patent: Jul. 13, 1999

[54] DENTAL AND SURGICAL HANDPIECE WITH DISPOSABLE CARTRIDGE

[75] Inventor: Paul Dorman, Fort Worth, Tex.

[73] Assignee: Healthpoint, Ltd., San Antonia, Tex.

[21] Appl. No.: 09/105,675

[22] Filed: Jun. 26, 1998

Related U.S. Application Data

[63] Continuation-in-part of application No. 08/567,473, Dec. 5, 1995, Pat. No. 5,772,435.

[51] Int. Cl.$^6$ ........................................................ A61C 1/08
[52] U.S. Cl. ............................ 433/126; 433/132; 433/115
[58] Field of Search .................... 433/114, 126, 433/127, 132, 115

[56] References Cited

U.S. PATENT DOCUMENTS

| | | | |
|---|---|---|---|
| 2,090,885 | 8/1937 | Clark | 433/126 |
| 2,785,464 | 3/1957 | Hoffmeister | 32/27 |
| 3,376,084 | 4/1968 | McKee | 308/184 |
| 3,418,715 | 12/1968 | Ellis | 32/26 |
| 3,469,318 | 9/1969 | Saffir | 32/27 |
| 3,653,127 | 4/1972 | Ballarfd | 32/43 |
| 3,826,004 | 7/1974 | Gracefo | 32/58 |
| 3,909,946 | 10/1975 | Watanabe | 433/126 |
| 3,949,748 | 4/1976 | Malmin | 128/213 |
| 3,955,284 | 5/1976 | Balson | 433/126 X |
| 4,021,917 | 5/1977 | Nakanishi | 32/27 |
| 4,211,009 | 7/1980 | Leonard | 433/126 |
| 4,219,330 | 8/1980 | Jaremus | 433/126 |
| 4,255,143 | 3/1981 | Schuss et al. | 433/126 |
| 4,266,933 | 5/1981 | Warden et al. | 433/82 |
| 4,277,236 | 7/1981 | Kurz | 433/3 |
| 4,470,812 | 9/1984 | Martens et al. | 433/85 |
| 4,792,304 | 12/1988 | Schuss et al. | 433/126 |
| 4,921,424 | 5/1990 | Kimura | 433/126 X |
| 5,252,067 | 10/1993 | Kakimoto | 433/126 X |
| 5,306,147 | 4/1994 | Dragan et al. | 433/89 |
| 5,352,119 | 10/1994 | Sakurai | 433/126 X |
| 5,538,425 | 7/1996 | Reeves et al. | 433/126 X |
| 5,571,012 | 11/1996 | Witherley et al. | 433/126 X |
| 5,772,435 | 6/1998 | Dorman | 433/126 |
| 5,797,743 | 8/1998 | Bailey | 433/126 |

*Primary Examiner*—Nicholas D. Lucchesi
*Attorney, Agent, or Firm*—Zarley, McKee, Thomte, Voorhees & Sease

[57] ABSTRACT

A dental and surgical handpiece with disposable cartridge of the present invention includes a reusable handpiece and a disposable cartridge. The disposable cartridge contains all the major moving parts that provide torque and RPM for high speed dental drilling. The disposable cartridge detachably couples with the head of the reusable handpiece. The handpiece can be heat sterilized after the disposable cartridge is removed. The performance of the handpiece is not reduced by the sterilization since the turbine and bearings are contained in the disposable cartridge.

10 Claims, 3 Drawing Sheets

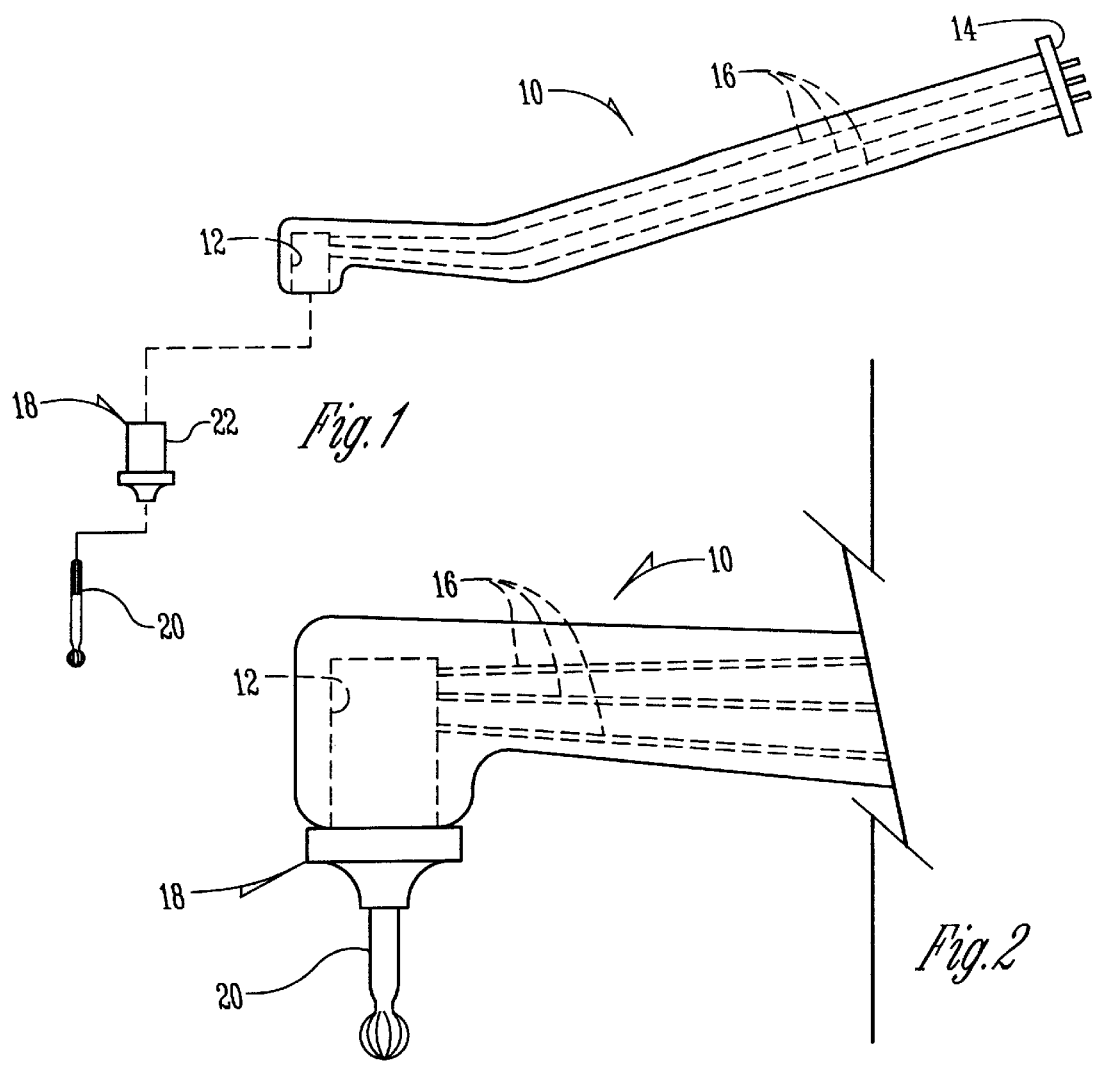
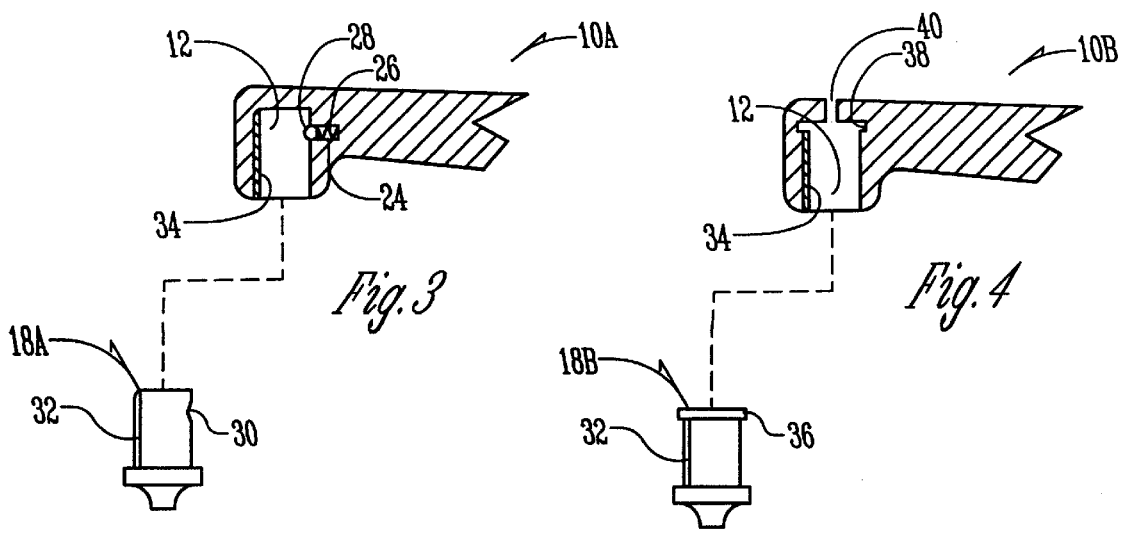

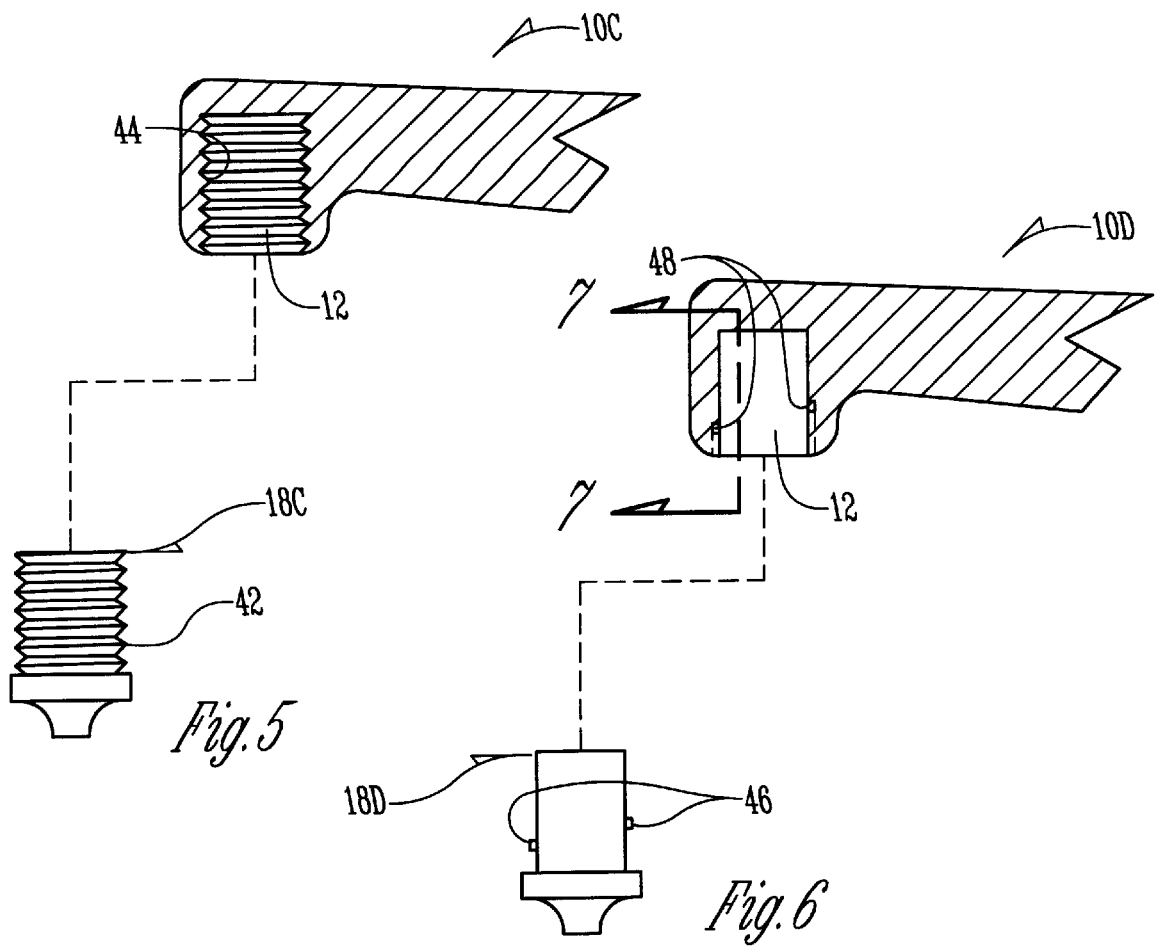
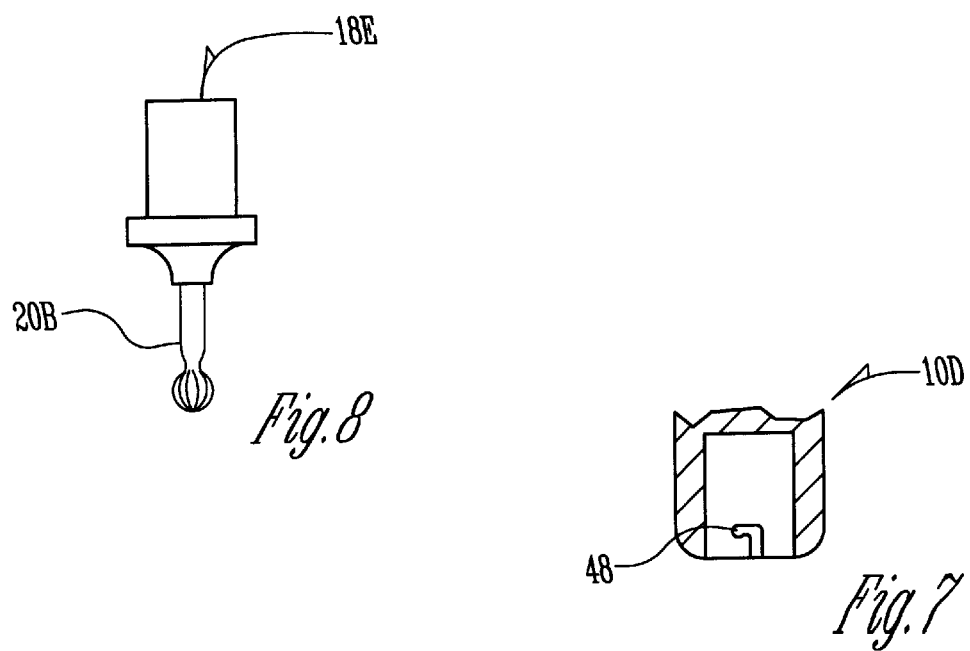

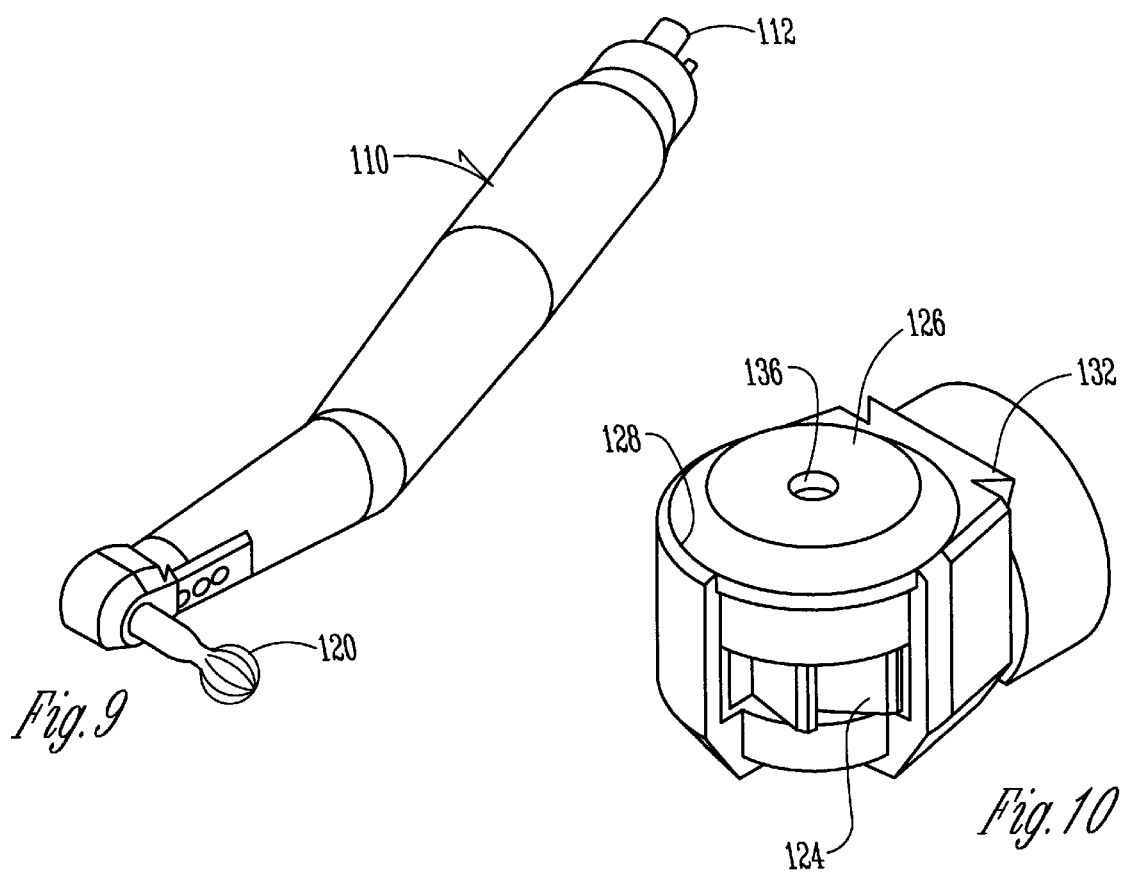
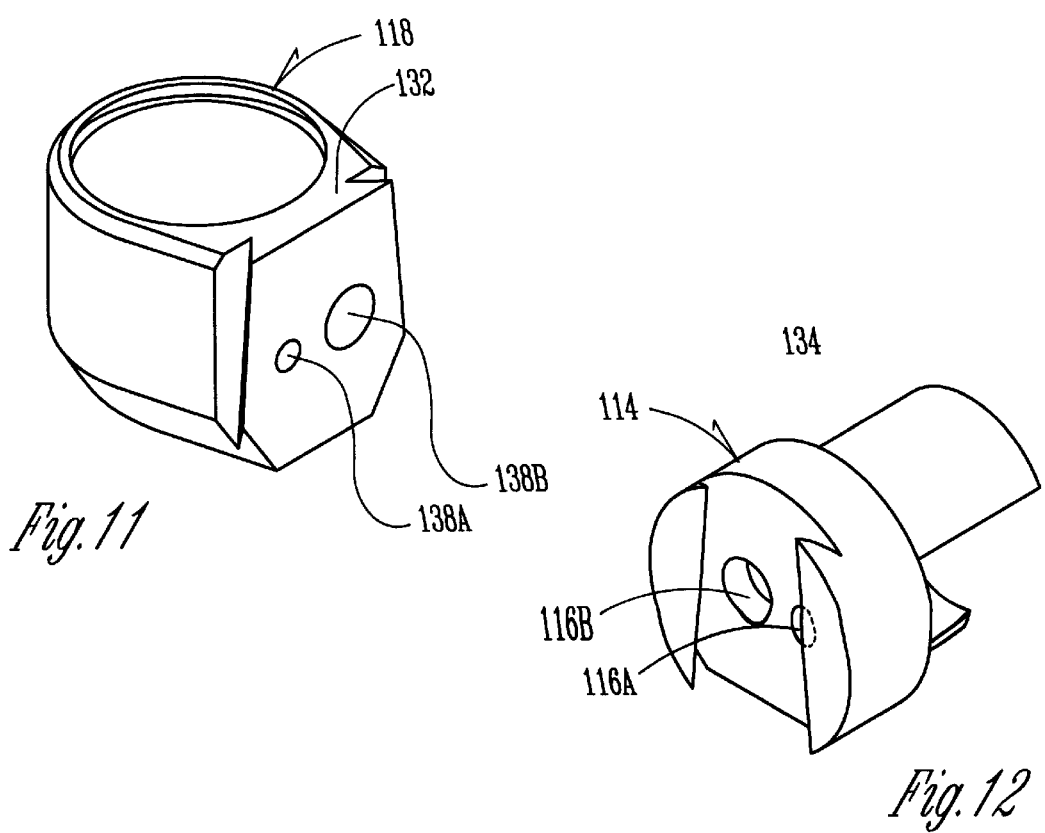

DENTAL AND SURGICAL HANDPIECE WITH DISPOSABLE CARTRIDGE

CROSS-REFERENCE TO A RELATED APPLICATION

This application is a continuation-in-part of U.S. patent application Ser. No. 08/567,473 filed Dec. 5, 1995, now U.S. Pat. No. 5,772,435.

BACKGROUND OF THE INVENTION

1. Field of the Invention

The present invention relates to dental and surgical instruments. More particularly, the present invention relates to a handpiece having a disposable cartridge assembly containing a turbine, shaft and bearing.

2. Problems in the Art

According to data released by the American Dental Association, infection control is the second largest area of concern to dentists. The rise in concern of infection control is in a large part due to recent documentation which demonstrates that disease can be transmitted in the dental office by blood and saliva retained in the turbine, shaft and bearings of a high speed handpiece. Infection control, specifically with a high speed handpiece, has become a public concern after reports of patients reportedly contracting the HIV virus at their dentist office. Additional research links nosocomial infections in the dentist office directly to the use of the high speed handpiece.

The concern of infection control is not limited to the transmission of the HIV virus, but also includes the transmission of Tuberculosis, Pneumonia, Influenza, the common cold, Oral Herpes, and possibly the transmission of Hepatitis B.

As a result of the growing concern of transmission of diseases between patients, dentists have had to conform to more stringent cleaning and sterilization procedures for their handpieces. Included in those procedures is autoclaving handpieces after each patient. Autoclaving is a process of sterilization that heats the handpieces above 250° F. for a certain amount of time to kill germs. A "cool-down" period is then required before the handpiece can be used on another patient.

The combination of the air, water, and the high speed rotation of the drilling bur creates an aerosol, which includes tissue, blood, and saliva, that is drawn up into the turbine, shaft, and bearings of the handpiece along with the residual lubricants left in the handpiece. For proper cleaning of a typical prior art handpiece, the drill bur must be removed from the handpiece. The top is then removed from the head of the handpiece, generally by unscrewing a cover plate, and the turbine, shaft and bearings are then removed and then cleaned and autoclaved. Damage to the various parts can result if care is not taken. The handpiece is easily cleansed and autoclaved since it has no small intricate moving parts once the turbine, shaft and bearings have been removed.

Currently, it is difficult to properly clean the complete handpiece assembly prior to autoclaving. While the turbine, shaft, and bearings are separable from the tube structure of the handpiece, they are difficult to clean and sterilize due to their small intricate design. The empty handpiece is more easily cleaned and sterilized.

The residual debris found in the mechanisms of the handpiece can contain and trap microorganisms which were drawn up into the turbine, shaft, and bearings. The microorganisms can later migrate back down the drill bur or into the handpiece channels where they can harbor, multiply, and be forcibly introduced into the body tissues of subsequent patients.

Since the turbine, shaft, and bearings are not changed from patient to patient, cross contamination is probable.

The transmittal of organisms associated with diseases such as Tuberculosis, Oral Herpes, Hepatitis and HIV via the handpiece assembly is of prime concern due to the potential introduction of high concentrations of microorganisms into the oral cavity.

A conventional high-speed dental handpiece assembly is connected at one end to a base coupler assembly which provides fluid and air under pressure. The opposite end (head) contains the chamber housing the components necessary to provide high speed rotation under air pressure (typically, the turbine, shaft, and bearings). Conventionally, the air pressure rotatably drives the turbine which contains a shaft with a chuck designed to grip the cutting bur. This design normally requires a chuck tool to tighten the chuck onto the bur and to loosen the chuck when removing the bur. The chuck can be over tightened distorting and causing damage to the chuck. Due to under tightening, or slight variances in bur shank size, the bur can slip, and not rotate or cut properly. Also, debris can get lodged in the chuck. A dentist can waste a significant amount of time looking for the bur tool, untightening the chuck, replacing a cutting bur, retightening the chuck, and removing the bur tool. If this procedure is not performed correctly, or if the shank of the bur is undersized, or if debris is present in the chuck, the cutting bur may slip and not cut properly.

The extreme heat of autoclaving causes any remaining lubricants, blood, tissue, and saliva to bake into the turbine, shaft and bearings, eventually causing "lock-up" of the internal moving parts.

It can be seen that the cleaning and sterilization process is costly and time consuming. Not only is the procedure itself costly and time consuming to a dentist, but the autoclaving and cool-down between patients requires additional handpieces. The performance of the handpiece assembly is reduced as repeated autoclaving adds to the build-up of baked on debris which can result in smaller patient loads due to scheduling around autoclaving or increased personnel to clean and autoclave on a more rapid interval.

FEATURES OF THE INVENTION

A general feature of the present invention is the provision of a dental handpiece with a disposable cartridge assembly.

A further feature of the present invention is the provision of a dental handpiece with disposable cartridge assembly including a turbine, shaft, and bearing.

A further feature of the present invention is the provision of a dental handpiece with disposable cartridge assembly which can be easily inserted and removed from the dental handpiece.

A further feature of the present invention is the provision of a dental handpiece with disposable cartridge assembly which provides the user with an easy method of sanitizing the dental instrument.

An optional feature of the present invention is the provision of a dental handpiece with disposable cartridge assembly which includes a drilling bur.

An optional feature of the present invention is the provision of a dental handpiece with disposable cartridge assembly which includes a removing tool.

An optional feature of the present invention is the provision of a dental handpiece with disposable cartridge assembly which is secured to the dental handpiece by any number of fastening means.

An optional feature of the present invention is the provision of a dental handpiece with disposable cartridge assembly which is secured to the dental handpiece with a spring loaded ball detent.

An optional feature of the present invention is the provision of a dental handpiece with disposable cartridge assembly which is secured to the dental handpiece with a compression snap-in device.

An optional feature of the present invention is the provision of a dental handpiece with disposable cartridge assembly which is secured to the dental handpiece with a threaded screw in fastening means.

An optional feature of the present invention is the provision of a dental handpiece with disposable cartridge assembly which is secured to the dental handpiece by a quarter turn lock in position thread fastening means.

These as well as other features will become apparent from the following specification and claims.

SUMMARY OF THE INVENTION

The dental and surgical tool of the present invention is comprised of a handpiece and a disposable cartridge removably coupled to the handpiece. The cartridge houses the moving parts of the tool which is preferably a fluid powered tool. The moving parts may include a turbine, shaft, bearings, seals, and accessories required to hold a drilling bur. After using the tool, the user may sterilize the tool by simply removing and disposing of the cartridge and cleaning the handpiece which includes no moving parts. Before using the tool again, the user inserts a new cartridge into the handpiece.

BRIEF DESCRIPTION OF THE DRAWINGS

FIG. 1 shows an embodiment of a dental handpiece, disposable cartridge, and drill bur of the present invention.

FIG. 2 shows an enlarged view of the dental handpiece with the disposable cartridge inserted.

FIGS. 3–7 show various means for securing the disposable cartridge assembly to the dental handpiece.

FIG. 8 shows an alternative disposable cartridge assembly which includes a drill bur.

FIG. 9 is a perspective view of an embodiment of the dental tool of this invention wherein the cartridge slide-lockingly mounts to the head end of the handpiece.

FIG. 10 is an enlarged perspective view of the cartridge and handpiece of FIG. 9 and shows the structure for slide-lockingly detachably mounting the cartridge to the handpiece.

FIG. 11 is an enlarged perspective view of the cartridge housing.

FIG. 12 is an enlarged perspective view of the portion of the handpiece which detachably interlocks with the cartridge.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalences which may be included within the spirit and scope of the invention.

The present invention pertains to a high speed rotary cutting tool of the type usable in dental and surgical procedures, and to a disposable cartridge containing all the moving, working parts that install into the chamber (head) of the handpiece forming the handpiece assembly.

FIG. 1 shows a dental handpiece 10 with a disposable cartridge 18 of the present invention. A handpiece 10 is shown having a cavity 12 formed in one end of the handpiece 10. The opposite end of the handpiece 10 includes a base coupler assembly 14 which connects to a source of fluid power (not shown), typically pressurized air. Between the base coupler 14 and the cavity 12 are a number of air passages 16 (shown by single dashed lines in FIG. 1) which provide a passageway for the compressed air to flow between the fluid power source and the cavity 12. Note that the handpiece 10 itself does not have any moving parts.

Also shown in FIG. 1 is a disposable cartridge 18 which is adapted to be removably inserted into the cavity 12 of the handpiece 10. The cartridge 18 includes the moving parts which are powered by the fluid power source. Contained within the disposable cartridge 18 is a turbine, shaft, bearings, seals, and accessories required to hold a drilling bur and to provide spacing (loading) for the bearings. When the disposable cartridge 18 is inserted into the cavity 12 (FIG. 2), the air passageways 16 will be in communication with the turbine so that the fluid power source is able to drive the turbine and therefore power the dental handpiece. FIG. 1 also shows a drill bur 20 which is inserted into a chuck mechanism (not shown) contained within the disposable cartridge 18. With the drill bur 20 coupled to the chuck and the cartridge 18 inserted into the cavity 12 (FIG. 2), the drill bur can be rotated and powered by the fluid power source.

The disposable cartridge 18 comprises an outer housing 22 designed to contain the moving parts and to fasten to the handpiece 10 within the cavity 12. The outer housing 22 of the cartridge 18 is preferably round shaped although other shapes could be used within the scope of the invention.

The disposable cartridge 18 can be secured to the handpiece 10 in any number of ways. FIGS. 3–7 show just a few specific examples of ways to secure the cartridge 18 within cavity 12 of the handpiece 10.

FIG. 3 shows a handpiece 10A and a cartridge 18A adapted to be secured together using a spring loaded ball detent fastener. The handpiece 10A includes a hole 24 formed perpendicular to the cavity 12. Within the hole 24 are a spring 26 and a ball 28. The ball 28 is movable within the hole 24 and is biased outward by the spring 26. The cartridge could also be secured by placement of the ball and spring in the cartridge and the detent in the handpiece. The disposable cartridge 18A includes a recess 30. When the cartridge 18A is inserted within the cavity 12, the ball 28 will be biased against the cartridge 18 within recess 30 securing the cartridge in place. The cartridge 18A also includes a tongue 32 which comes into engagement with a groove 34 formed in the handpiece 10A so that the cartridge 18 will not rotate relative to the handpiece 10A.

FIG. 4 shows a handpiece 10B and a disposable cartridge 18B adapted to be secured together using a compression snap-in fastener. The snap-in fastener 36 could be in the form of a "G" ring, spring ring or snap ring. The cartridge 18B includes a projection 36 extending around the perimeter of the top of the cartridge 18B. The handpiece 10B includes a matching slot 38 formed in the cavity 12. To secure the cartridge 18B to the handpiece 10B, the cartridge is pressed into the cavity compressing the projection 36 until it reaches the slot 38. The cartridge 18B includes a tongue 32 which engages with a matching groove 34 formed in the cavity 12 to prevent the cartridge from rotating relative to the handpiece 10B. To remove the disposable cartridge 18B, a removal tool is used to push the cartridge 18B out of the handpiece 10B by inserting the tool through a hole 40 formed in the handpiece 10B.

FIG. 5 shows a handpiece 10C and a disposable cartridge 18C adapted to be secured together using a threaded fastener. The disposable cartridge 18C includes male threads 42 which are adapted to be screwed into female threads 44 which are formed in the handpiece 10C.

FIG. 6 shows a handpiece 10D and a disposable cartridge 18D adapted to be secured together using a quarter turn lock-in position threads or a cam type fastener. The cartridge 18D includes two projections 46 adapted to fit within slots 48 which are formed in the handpiece 10D. The slots 48 are L-shaped as shown in FIG. 7. After the cartridge 18D is inserted into the cavity 12 of handpiece 10D, the cartridge 18 is rotated to secure the cartridge within the cavity 12.

FIG. 8 shows an alternative disposable cartridge 18E. The disposable cartridge 18E includes a drill bur 20B which is formed as part of the disposable cartridge 18E such that when the cartridge 18E is inserted and removed, the drill bur 20B is inserted and removed with the cartridge 18E. In this way, the drill bur 20B is disposable along with the cartridge 18E. Also, there is no need for a chuck or chuck tool. In this embodiment, the shaft of the drill bur 20B may be integral to the turbine of the cartridge.

Since the disposable cartridge 18 is a separate assembly from the handpiece 10, it is disposable where as the handpiece 10 is reused after it is cleaned and sterilized. Thus, the handpiece maintenance is reduced due to the prevention of an accumulation of clogging, debris baked into the turbine, shaft, and bearing assembly. Moreover, the patient to patient cross contamination from microorganisms drawn into the assembly and later forced out of the assembly is reduced or eliminated since the cartridge assembly is disposed of after it is used.

The disposable cartridge 18 is designed to quickly lock into the handpiece 10 to facilitate quick assembly, removal and disposal of the cartridge 18. The design of the cartridge 18 allows for the quick removal and disposal of all parts that are difficult to clean. The reused part of the handpiece does not contain any small moving parts that are difficult to clean and subject to a "baked on" build-up resulting from autoclaving the handpiece.

The new disposable cartridge 18 could be delivered to the dentist in a pre-sterilized condition, packaged and ready for easy placement (and locking) into the head of the reusable handpiece.

FIGS. 9–12 illustrate another embodiment of the present invention in which the cartridge 118 slide-lockingly and detachably couples with the elongated handpiece 110. The handpiece 110 has a power input end 112 which preferably receives fluid power from a conventional source of pressurized fluid (not shown). A power output end 114 resides generally opposite the input end 112 and includes at least one air power port 116A, 116B therein where the handpiece 110 operatively terminates. A groove 134 in the handpiece 110 surrounds the fluid power port 116A, 116B and provides the means for slide-lockingly and detachably coupling the cartridge 118 to the handpiece 110.

The cartridge 118 is preferably disposable and has a housing 122 with a turbine 124 rotatably mounted or journaled therein. The turbine 124 drivingly engages a tool 120, such as a bur, drill, or the like. A snap-on retaining cap 126 sealingly and frictionally fits over an opening 128 in the housing 122 adjacent the turbine 124. The shank of the tool 120 extends into, and preferably through, a hole 136 formed in the retaining cap 126. The housing 122 has at least one fluid port 138A, 138B which is in fluid communication with the turbine 124. The air ports 138A, 138B on the cartridge 118 are adapted to register with the fluid ports 116A, 116B, respectively, on the handpiece 110.

A tongue 132 is formed on the surface of the cartridge 118, preferably an exterior surface. A mating groove 134 is formed on the exterior surface of the handpiece 110. The groove 134 extends transversely with respect to the longitudinal axis of the handpiece 110. The groove 134 and the tongue 132 have complementary dovetailed shapes for slide-lockingly receiving each other. Both the groove 134 and tongue 132 are tapered from one end to the other. This feature provides the positive location needed to register the ports 116A, 116B, 138A, 138B with each other when the cartridge 118 fully couples with the handpiece 110 so that the tongue 132 and groove 134 matingly interlock. A snug sliding fit is desirable so that the coupling cannot be inadvertently broken. Of course, the tongue 132 could be located on the handpiece 110 and the groove 134 could be located on the cartridge 118 without detracting from the invention.

Thus, the cartridge 118 is mechanically and fluidly coupled with the handpiece 110. The tongue and groove structure prevents the cartridge 118 from rotating relative to the handpiece 110.

The preferred embodiments of the present invention have been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A dental tool comprising:
   an elongated handpiece having a power input end and a power output end generally opposite the power input end;
   a dental tool cartridge slide-lockingly and detachably coupled where the power output end of the handpiece operatively terminates; and
   a tongue being formed on an exterior surface of one of the cartridge and the handpiece and a groove for matingly interlocking with the tongue being formed on the other of the cartridge and the handpiece;
   the groove having a dovetailed shape.

2. The dental tool of claim 1 wherein the cartridge is disposable.

3. The dental tool of claim 1 wherein the groove extends transversely with respect to a longitudinal axis of the handpiece.

4. The dental tool of claim 1 wherein the groove has opposite ends, and a width that is tapered smaller from one of the ends to the other of the ends.

5. The dental tool of claim 1 wherein the tongue has opposite ends, and a width that is tapered smaller from one of the ends to the other of the ends.

6. The dental tool of claim 1 comprising a fluid power port on the power output end of the handpiece and a fluid power port on the cartridge which registers with the fluid power port on the power output end of the handpiece when the cartridge is fully coupled with the handpiece.

7. The dental tool of claim 6 wherein the cartridge has a passage therein fluidly operatively connecting the port of the power output end of the handpiece with a turbine mounted in the cartridge.

8. The dental tool of claim 1 wherein the cartridge includes a drilling bur.

9. A dental tool comprising:

an elongated handpiece having a power input end and a power output end generally opposite the power input end;

a dental tool cartridge slide-lockingly and detachably coupled where the power output end of the handpiece operatively terminates; and a tongue being formed on an exterior surface of one of the cartridge and the handpiece and a groove for matingly interlocking with the tongue being formed on the other of the cartridge and the handpiece;

the tongue having a dovetailed shape adapted to slidingly fit snugly in the groove.

10. A dental tool comprising:

an elongated handpiece having a power input end and a power output end generally opposite the power input end;

a dental tool cartridge slide-lockingly and detachably coupled where the power output end of the handpiece operatively terminates;

the cartridge having a substantially planar exterior surface thereon for mechanically engaging and fluidly coupling with a substantially planar surface on the handpiece; and an air power port on the power output end of the handpiece intersecting the planar surface of the handpiece and registering with an air power port on the cartridge which is in communication with an air turbine housed within the cartridge;

whereby upon mechanical engagement, the planar surfaces of the cartridge and the handpiece sealingly engage each other so as to define a sealed fluid coupling surrounding the air power ports.

* * * * *